United States Patent [19]
Chen et al.

[11] Patent Number: 5,849,846
[45] Date of Patent: *Dec. 15, 1998

[54] BALLOONS FOR MEDICAL CATHETERS

[75] Inventors: Ziyun Chen, Santa Clara; Tai C. Cheng, Mounain View; Jeong S. Lee, Diamond Bar; Ketan P. Muni; Udayan Patel, both of San Jose; Robert P. Saltman, Redwood City, all of Calif.

[73] Assignee: Advanced Cardiovascular Systems, Inc., Santa Clara, Calif.

[*] Notice: This patent issued on a continued prosecution application filed under 37 CFR 1.53(d), and is subject to the twenty year patent term provisions of 35 U.S.C. 154(a)(2).

[*] Notice: The term of this patent shall not extend beyond the expiration date of Pat. No. 5,554,120.

[21] Appl. No.: 476,101

[22] Filed: Jun. 6, 1995

Related U.S. Application Data

[63] Continuation-in-part of Ser. No. 280,764, Jul. 25, 1994, Pat. No. 5,554,120.

[51] Int. Cl.⁶ .......................... A61M 25/00; A61M 25/10; A61M 29/02
[52] U.S. Cl. .......................... 525/166; 525/176; 525/179; 525/183; 525/476; 604/96; 604/280
[58] Field of Search .................................. 525/166, 176, 525/445, 426, 179, 183; 604/96, 280

[56] References Cited

U.S. PATENT DOCUMENTS

| | | | |
|---|---|---|---|
| Re. 28,982 | 9/1976 | Crawford et al. | 260/873 |
| Re. 32,983 | 7/1989 | Levy | 428/36.92 |
| 3,317,631 | 5/1967 | Rees | 260/854 |
| 3,591,659 | 7/1971 | Brinkmann et al. | |
| 3,624,272 | 11/1971 | Rees | 260/78.5 |
| 3,651,014 | 3/1972 | Witsiepe | 260/75 R |
| 3,718,715 | 2/1973 | Crawford | 260/873 |
| 3,763,109 | 10/1973 | Witsiepe | 260/75 R |
| 3,766,146 | 10/1973 | Witsiepe | 260/75 R |
| 3,793,262 | 2/1974 | Legothetis | 260/86.7 |
| 3,835,098 | 9/1974 | Morton Brown et al. | 260/75 N |
| 3,925,326 | 12/1975 | Legothetis | 260/78.5 R |
| 4,022,748 | 5/1977 | Schlichting | 260/40 |
| 4,026,967 | 5/1977 | Flexman, Jr. et al. | 525/52 |
| 4,034,013 | 7/1977 | Lane | 260/835 |
| 4,172,859 | 10/1979 | Epstein | 428/402 |
| 4,174,358 | 11/1979 | Epstein | 525/183 |
| 4,221,703 | 9/1980 | Hoeschele | 260/45.9 |
| 4,254,774 | 3/1981 | Boretos | 128/348 |
| 4,275,180 | 6/1981 | Clarke | 525/173 |
| 4,284,540 | 8/1981 | Iida et al. | 26/22 R |
| 4,317,764 | 3/1982 | Sheer | 524/449 |
| 4,322,335 | 3/1982 | Nield | 523/522 |
| 4,410,482 | 10/1983 | Subramanian | 264/515 |
| 4,444,817 | 4/1984 | Subramanian | 428/36 |
| 4,490,421 | 12/1984 | Levy | 428/35 |
| 4,514,620 | 4/1985 | Cheng et al. | 219/553 |
| 4,556,705 | 12/1985 | McCready | 528/289 |
| 4,680,344 | 7/1987 | Coker | 525/176 |
| 4,737,440 | 4/1988 | Uno et al. | 430/227 |
| 4,753,980 | 6/1988 | Deyrup | 524/369 |
| 4,758,629 | 7/1988 | Deyrup et al. | 525/194 |
| 4,820,349 | 4/1989 | Saab | 128/344 |
| 4,871,810 | 10/1989 | Saltman | 525/133 |
| 4,906,241 | 3/1990 | Noddin et al. | 606/194 |
| 4,906,244 | 3/1990 | Pinchuk et al. | 606/194 |
| 4,946,743 | 8/1990 | Winter | 428/249 |
| 4,960,410 | 10/1990 | Pinchuk | 604/96 |
| 4,963,313 | 10/1990 | Noddin et al. | 264/573 |
| 4,964,409 | 10/1990 | Tremulis | 128/657 |
| 5,017,325 | 5/1991 | Jackowski et al. | 264/521 |
| 5,041,125 | 8/1991 | Montano, Jr. | 606/192 |
| 5,091,459 | 2/1992 | Howe | 524/456 |
| 5,108,415 | 4/1992 | Pinchuk et al. | 606/194 |
| 5,115,012 | 5/1992 | Howe | 524/456 |
| 5,128,404 | 7/1992 | Howe | 524/456 |
| 5,195,969 | 3/1993 | Wang et al. | 604/96 |
| 5,195,970 | 3/1993 | Gahara | 604/96 |
| 5,226,887 | 7/1993 | Farr et al. | 604/96 |
| 5,260,387 | 11/1993 | Boundy et al. | 525/444 |
| 5,270,086 | 12/1993 | Hamlin | 428/35 |
| 5,290,306 | 3/1994 | Trotta et al. | 606/194 |
| 5,306,246 | 4/1994 | Sahatjian, et al. | 604/96 |
| 5,315,747 | 5/1994 | Solar | 29/447 |

FOREIGN PATENT DOCUMENTS

| | | | |
|---|---|---|---|
| 0 457 456 A1 | 11/1991 | European Pat. Off. | A61M 25/00 |
| 0 531 117 A2 | 3/1993 | European Pat. Off. | B29C 55/26 |
| 0 566 755 A1 | 10/1993 | European Pat. Off. | A61L 29/00 |
| 6-145483 | 5/1994 | Japan . | |
| 7-18088 | 1/1995 | Japan . | |
| 1241168 | 7/1971 | United Kingdom . | |
| 2015014 | 9/1979 | United Kingdom | C08L 67/02 |
| WO 90/01345 | 2/1990 | WIPO | A61L 2/00 |
| WO 91/17788 | 11/1991 | WIPO | A61M 29/00 |
| WO 92/08512 | 5/1992 | WIPO | A61M 29/00 |
| WO 92/19440 | 11/1992 | WIPO | B29C 49/00 |

*Primary Examiner*—Patricia A. Short
*Attorney, Agent, or Firm*—Fulwider Patton Lee & Utecht, LLP

[57] ABSTRACT

A catheter and/or balloon for a medical catheter is formed from a blend of polymeric components, including a first crystalline polymeric component and a second softening polymeric component. The polymeric material can also include a third compatibilizing agent to facilitate blending the first two polymeric components together. The first polymeric component can be a polyester or a polyamide, and the second polymeric component can be a polyolefin, or an ethylene copolymer. The third polymeric component is preferably an ethylene copolymer containing a reactive group that forms a covalent bond with the first polymeric component. The polymeric material forming the balloon or catheter also can include a catalyst to catalyze a reaction between the compatibilizing ethylene copolymer and the second polymer component. The second, softening polymeric component can also include a silane coupling agent, to provide a reactive softening copolymer that bonds with the first strong polymeric component, to provide increased flexibility of catheters and balloons formed from the polymeric components. The properties of the balloon and catheter formed from the polymeric material can be enhanced by crosslinking by irradiation of the polymeric material.

40 Claims, 1 Drawing Sheet

5,849,846

BALLOONS FOR MEDICAL CATHETERS

RELATED APPLICATIONS

This application is a continuation-in-part of U.S. patent application Ser. No. 08/280,764, filed Jul. 25, 1994, now U.S. Pat. No. 5,554,120.

FIELD OF THE INVENTION

This invention relates generally to balloons for medical catheters and, more particularly, to new and improved medical balloon dilatation catheters, and medical devices such as catheters and dilatation balloons formed from an improved composition of polymeric materials, whereby the medical balloon dilatation catheters, catheters and dilatation balloons are provided with improved performance characteristics.

DESCRIPTION OF RELATED ART

Catheters are well known for their usefulness in medical applications and in particular angioplasty procedures, for opening blood vessels or other passageways in the body that may be blocked by obstructions or stenosis. Dilatation catheters are generally formed from thin, flexible tubing having an inflatable balloon at or near a distal tip of the tubing that can be inflated with fluid pressure communicated to the balloon through a lumen of the tubing. In a typical angioplasty procedure, the balloon dilatation catheter is passed through the vasculature to the location of a stenosis in an artery, and the balloon is inflated to a predetermined size and shape to open the blocked artery.

It is desirable for balloons of balloon dilatation catheters to be capable of inflating to a diameter of typically two to four times their uninflated diameter in order to be able to open an obstructed vessel. Other desirable properties of balloons for such balloon dilatation catheters include strength, softness, flexibility and a thin, low profile which are important for achieving the performance characteristics of folding in an uninflated state, tracking, crossing and recrossing the area of the obstruction or stenosis in a vessel in an uninflated state. In addition, properties of burst strength, compliance, and fatigue have been increasingly important in the continuing effort to create thinner, lower profile balloons for balloon dilatation catheters with an ability to track, cross and recross increasingly narrow passages in obstructed vessels. For purposes of this description, the ability to cross is defined as the ability of a balloon of a balloon dilatation catheter to pass through a stenosis; the ability to recross is defined as the ability of the balloon of a balloon dilatation catheter to pass through a stenosis more than once, or to pass through more than one stenosis; and the ability to track is defined as the ability of balloon of a balloon dilatation catheter to pass over a guidewire through the tortuous curves of the vasculature, in being guided to and from the location of a stenosis.

Polymeric materials that have been used for making medical devices, catheters, dilatation catheters, and balloons for balloon dilatation catheters include polyethylene, polyolefins, polyvinyl chloride, polyester, polyamide, polyethylene terephthalate (PET), polyamides, nylon, polyurethane, and the like. Balloons made of soft polyolefin or ethylene copolymers materials are typically foldable, and track and cross well, so that they can often be used more than once, and can be used to cross multiple lesions. However, such balloons also commonly have high balloon compliance and low burst strengths, with ratings of rated burst pressure of about 8–9 atm, and a mean burst pressure of about 10–15 atm. Balloons made from polyethylene terephthalate (PET) are commonly stronger, with a higher rated burst pressure of about 14–18 atm, and a mean burst pressure of about 18–25 atm. However, dilatation catheter balloons made of PET are generally stiff, not readily foldable and refoldable, and are susceptible to acquiring defects from mechanical handling.

Examples of prior art compositions that may be suitable in forming medical devices such as catheters, dilatation catheters, and balloon materials for use in angioplasty procedures include U.S. Pat. No. 4,753,980 (Deyrup); U.S. Pat. No. 4,172,859 (Epstein); U.S. Pat. No. 5,091,478 (Saltman); U.S. Pat. No. 5,306,246 (Sahatjian et al.); U.S. Pat. No. 4,254,774 (Boretos); U.S. Pat. No. 4,964,409 (Tremulis); and U.S. Pat. No. 5,017,325 (Jackowski et al.), all of which are incorporated herein by reference. These references are presented by way of example only and are not intended to be exhaustive of the prior art.

It would be desirable to provide a polymeric blend for balloons for balloon dilatation catheters with a combination of the best features of the softer balloon materials and the stronger balloon materials, including good flexibility, folding, track, cross and recross, with a thin, low profile, high resistance to fatigue, low compliance, and high burst strength, with a lower susceptibility to defects through mechanical handling, compared with balloons made from PET. The present invention meets these needs.

SUMMARY OF THE INVENTION

Briefly, and in general terms, the present invention provides a new and improved catheter and/or balloon formed from a blend of polymeric components that has enhanced rated and mean burst pressure characteristics, low compliance and excellent fatigue resistance, along with excellent folding and performance characteristics, such as track, cross and recross, allowing for construction of dilatation catheter balloons with the ability to cross multiple lesions.

Accordingly, by way of example and not necessarily by way of limitation, the invention provides for a catheter and/or balloon formed from a blend composition of a first crystalline polymeric component and a second softening polymeric component. When the first and second polymeric components are essentially incompatible in that they are immiscible, and do not normally bond together well, a third polymeric component, a compatibilizing agent, can be included in the balloon material to strengthen the interface between the two incompatible materials and to facilitate blending of the first two polymeric components. A fourth component, a catalyst, also can be optionally included in the blend composition to catalyze a reaction between the compatibilizing agent and the second, softening polymeric component.

The first polymeric component can generally consist of about 60 to 95 percent by weight of the total blend composition, and can comprise one or more polyester or polyamide polymers. In a presently preferred embodiment, the polyester polymer can be selected from polyesters prepared from the group of dicarboxylic acids selected from aromatic dicarboxylic acids having from 8 to 14 carbon atoms and aliphatic dicarboxylic acids having from 2 to 12 carbon atoms, and at least one glycol selected from the group consisting of glycols having the formula $HO(CH_2)_nOH$, where n is an integer from 2 to 10, neopentyl glycol and cyclohexane dimethanol. In an alternative embodiment, the first polymeric component can be one or more polyamides selected from branched or straight chain polyamides having a molecular weight of at least about 5000.

The second polymeric component generally has a Shore hardness less than 75 D, preferably less than 55 D, can consist of zero to about 40 percent by weight of the total blend composition, and can be one or more polymers selected from the group consisting of ethylene copolymers and polyolefins, the polyolefins having a density less than 0.93.

The third polymeric component generally can consist of from zero to about 40 percent by weight, and more preferably about 1 to 20 percent by weight, of the total balloon material blend, of a compatibilizing ethylene copolymer that can have the formula E/X/Y or E/Y, where E is ethylene. Most preferably, the third polymeric component consists of about 4 to 15 percent by weight of the total balloon material blend. X can consist of from zero to about 40 percent by weight of the third polymeric component, and more preferably from zero to about 10 percent by weight. X, if present, can be an $\alpha$, $\beta$-ethylenically unsaturated monomer derived from at least one of vinyl acetate, alkylacrylate, alkylmethacrylate, alkyl vinyl ether, carbon dioxide, sulfur dioxide, or mixtures thereof, where the alkyl groups contain 1–12 carbon atoms; and Y is an $\alpha$, $\beta$-ethylenically unsaturated monomer containing a reactive group that will form a covalent bond with the first polymeric component.

In a presently preferred embodiment, the first polymeric component comprises about 60–79 percent of the total blend composition, and can be selected from the group consisting of polyethylene-terephthalate, polybutylene-terephthalate, glycol modified polyethylene-terephthalate, 1,4-cyclohexylene dimethylene terephthalate/isophthalate copolymer, linear homopolymer esters derived from aromatic dicarboxylic acids and glycols of the general formula $HO(CH_2)_nOH$ where n is an integer from 2 to 10, and combinations thereof. In a presently preferred aspect of the invention, the second polymeric component is a softening ethylene copolymer comprising about 10–40 percent by weight of the total blend composition, and contains ethylene and at least one other monomer selected from the group consisting of $\alpha$, $\beta$-ethylenically unsaturated monomers, carbon monoxide, and sulfur dioxide.

In a presently preferred embodiment, in the third polymeric component, the compatibilizing agent, X, if present, can be selected from the group consisting of vinyl acetate, methylacrylate, ethylacrylate, butylacrylate, and methyl vinyl ether, and Y can be an $\alpha$, $\beta$-ethylenically unsaturated monomer containing a reactive group selected from the group consisting of epoxide, anhydride, isocyanate, or oxazoline. In one presently preferred embodiment, Y is selected from the group consisting of glycidyl acrylate, glycidyl methacrylate, and other epoxide containing copolymerizable monomers.

In one preferred embodiment, the softening ethylene copolymer can comprise one or more polymeric compounds having the formula E'X' or E'X'Y', where E' is ethylene, and is about 60–90 percent by weight of the ethylene copolymer, and where X' is about 10–40 percent by weight of the ethylene copolymer, and X' is selected from the group consisting of methylacrylate, ethylacrylate, propylacrylate, butylacrylate, and mixtures thereof, and Y', if present, is an $\alpha$, $\beta$-ethylenically unsaturated monocarboxylic acid, di-acid or anhydride comprising zero to about 15 percent, and most preferably about 1 to 5 percent, by weight of the ethylene copolymer. Examples of Y' include but are not limited to acrylic acid, methacrylic acid, fumaric acid and maleic anhydride. Where one of the X' or Y' monomers is an acid containing moiety, the polymer can also be at least partially neutralized with an ion selected from the group of sodium, potassium, zinc, lithium, calcium, magnesium, and ammonium.

In a currently preferred embodiment, the third polymeric component, the compatibilizing agent, comprises an ethylene copolymer in which E is ethylene, and comprises about 55 to 96 percent by weight, and most preferably about 92 to 96 percent by weight, of the compatibilizing agent; X, if present, is zero to about 40 percent by weight, and most preferably zero to about 10 percent by weight of the compatibilizing agent and can be selected from the group of methylacrylate, ethylacrylate, and butylacrylate; and Y can be selected from the group consisting of glycidyl acrylate and glycidyl methacrylate, and comprises about 0.5 to 10 percent by weight, and most preferably about 4 to 8 percent of the compatibilizing agent.

In a currently preferred embodiment, a fourth component, a polymeric catalyst component, also can optionally be included in the blend composition to catalyze a reaction between the compatibilizing agent and the second, softening polymeric component. In one currently preferred embodiment, the fourth component can comprise an aliphatic tertiary amine.

In another presently preferred aspect of the catheters and balloons, and the method of making the catheters and balloons of the invention, the catheter tubing material employed in making the balloons and catheters of the invention can advantageously be irradiated using ionizing radiation to provide improved balloon performance such as higher burst pressures.

In an alternate embodiment, the second, softening polymeric component can be modified with a silane coupling agent, such as vinyl silanes containing epoxide groups, to provide a reactive softening copolymer that will bond with the first strong polymeric component when they are blended together, and to allow reduction or elimination of the third, compatibilizing polymeric component, to provide increased flexibility of catheters and balloons formed from the polymeric components.

These and other aspects and advantages of the invention will become apparent from the following detailed description, and the accompanying drawings, which illustrate by way of example the features of the invention.

DETAILED DESCRIPTION OF THE PREFERRED EMBODIMENTS

Figure 1:
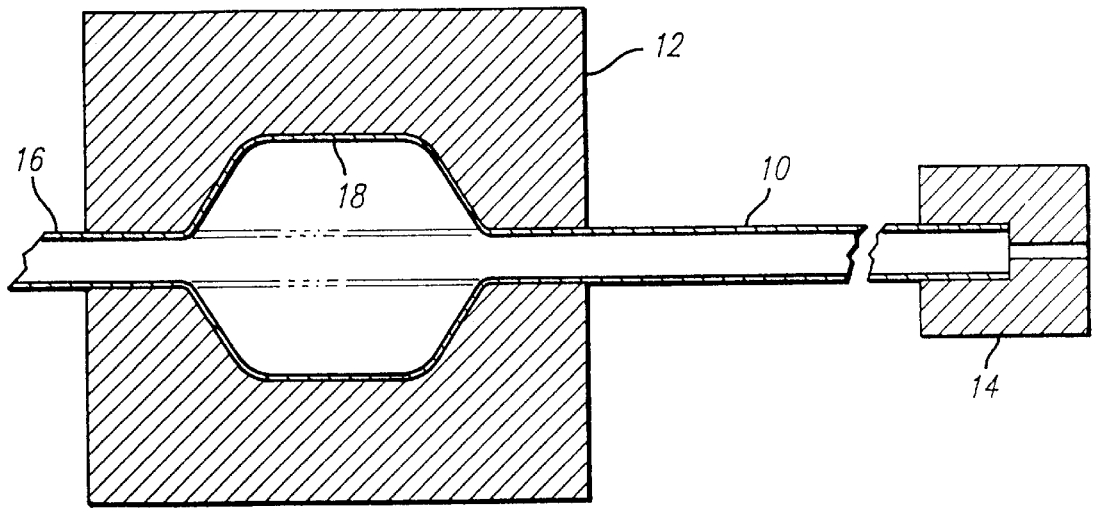
FIG. 1 illustrates an apparatus for performing an exemplary method of forming a dilatation catheter balloon in accordance with the principles of the present invention.

The present invention relates to catheters and balloons for medical catheters formed from a polymer blend having certain characteristics generally desirable in medical devices. The polymer blend described herein is particularly suitable for use in forming medical products such as catheters, dilatation catheters, and preferably balloons for use with catheters.

While dilatation catheter balloons made of soft polyolefin or ethylene copolymer materials have generally good performance characteristics, such balloons also commonly have high balloon compliance and low burst strengths. Dilatation catheter balloons made from strong polymeric materials such as polyethylene terephthalate (PET) have higher rated and mean burst pressures, but are generally stiff, not readily foldable and refoldable, and are susceptible to acquiring defects from mechanical handling. While the embodiments discussed herein refer generally to balloons made from polymeric materials, it is to be understood that the invention relates to catheters as well formed from the polymer blends as described.

The invention accordingly is embodied in a balloon for balloon dilatation catheters with a combination of the best features of the stronger balloon materials and the softer balloon materials. These include high burst strength and low compliance from the stronger balloon materials, and good flexibility, high resistance to fatigue, the ability to fold, track, cross and recross well, and with a lower susceptibility to defects through mechanical handling, compared with balloons made from PET. The balloon material is formed from a blend of polymeric components, comprising a strong polymeric component, a softening polymeric component that are generally incompatible, a compatibilizing polymeric component that forms a covalent bond with one or both of the first two polymeric components, and prevents the first two polymeric components from separating when formed as a balloon for a balloon dilatation catheter, and optionally a catalyst component to catalyze bonding between the compatibilizing polymeric component and the softening component.

The first polymeric component, component A, is preferably a relatively strong crystalline polymer, preferably comprising about 60–79 percent of the total blend composition, although blend compositions of the invention comprising as little as 60 percent or as much as 95 percent of the total blend composition may also be suitable. In one currently preferred embodiment, component A comprises PET, but can also comprise other polyesters, or polyamides. One or more other polyesters also can be used as component A, such as polyesters prepared from an aromatic dicarboxylic acid having from 8 to 14 carbon atoms and at least one glycol, including those having the formula $HO(CH_2)_nOH$ where n is an integer of 2 to 10, neopentyl glycol and cyclohexane dimethanol. The dicarboxylic acid may also be an aliphatic dicarboxylic acid having from 2 to 12 carbon atoms. Examples of other suitable polyesters include, but are not limited to, polybutylene-terephthalate (PBT), glycol modified PET (PETG), 1,4-cyclohexylene dimethylene terephthalate/isophthalate copolymer and other linear homopolymer esters derived from aromatic dicarboxylic acids and glycols of the general formula $HO(CH_2)_nOH$ where n is an integer from 2 to 10. Such aromatic dicarboxylic acids include isophthalic, bibenzoic, naphthalenedicarboxylic including the 1,5-; 2,6-; and 2,7-naphthalenedicarboxylic acids; 4,4'-diphenylenedicarboxylic acid; bis(p-carboxyphenyl) methane; ethylene-bis-p-benzoic acid; 1,4-tetramethylene bis(p-oxybenzoic) acid; ethylene bis(p-oxybenzoic) acid; 1,3-trimethylene bis(p-oxybenzoic) acid; and 1,4-tetramethylene bis(p-oxybenzoic) acid. Preferred glycols include ethylene glycol; 1,3-trimethylene glycol; 1,4-tetramethylene glycol; 1,6-hexamethylene glycol; 1,8-octamethylene glycol; 1,10-decamethylene glycol; 2,2-dimethyl-1,3-propane diol; 1,3-propylene glycol; 1,4-butylene glycol; neopentyl glycol and cyclohexane dimethanol.

Polyamides which are suitable for use as component A include branched or straight chain polyamides having a molecular weight of at least 5000, and commonly referred to as nylons, produced by condensation of equimolar amounts of a saturated dicarboxylic acid containing from 4 to 12 carbon atoms with a diamine, in which the diamine contains from 4 to 12 carbon atoms, or from polymers of amino acids containing from 4 to 12 carbon atoms. Examples of suitable polyamides include, but are not limited to, nylons such as polyhexamethylene hexanoamide (nylon 6,6), polyhexamethylene azelaamide (nylon 6,9), polyhexamethylene sebacamide (nylon 6,10), polyhexamethylene dodecanoamide (nylon 6,12), poly-11-amino-undecamoic acid (nylon 11), and poly-12-aminododecamoic nylon 12. Other polyamides that can be suitable include polyamide block copolymers such as those sold under the trade name "PEBAX" by Elf Atochem; polyamides including polyamides produced by the ring opening of lactams such as polycaprolactam (nylon 6), polylauryl lactam (nylon 12), polyundecyl lactam (nylon 11), and bis(paraaminocyclohexyl) methane dodecanoamide; and polyamides prepared by the copolymerization or terpolymerization of such polymers. The polyamides preferably have a melting point in excess of 160° C.

The second polymeric component, component B, is selected to be a softening polymer, preferably comprising about 10–40 percent by weight of the total balloon material composition, although blends of the balloon material comprising as little as zero percent of component B and as much as 40 percent of the total blend composition may also be suitable. In a currently preferred embodiment, component B comprises a softening polymer component having a Shore hardness less than 75 D, and preferably less than 55 D, and preferably comprises one or more elastomeric ethylene copolymers selected from the group of ethylene copolymers comprising ethylene and at least one other monomer selected from the group of α, β-ethylenically unsaturated monomers, carbon monoxide (CO), sulfur dioxide ($SO_2$). Component B most preferably comprises one or more elastomeric ethylene copolymers having the formula E'X' or E'X'Y', where E' is ethylene and comprises about 60 to 90 percent by weight of the ethylene copolymer, X' is acrylate or methacrylate monomer, comprising about 10 to 40 percent of the ethylene copolymer, and Y', if present, is an α, β-ethylenically unsaturated monocarboxylic acid, di-acid or anhydride comprising from zero to about 15 percent by weight of the ethylene copolymer. Examples of Y' include but are not limited to acrylic acid, methacrylic acid, fumaric acid and maleic anhydride. Other polymeric materials that may be suitable for use as component B include, but are not limited to polyetherimide esters such as those produced under the trade name "LOMOD" by General Electric; polyesters available from Dutch State Mines under the trade name "ARNITEL"; polyetheresters such as "HYTREL" produced by E. I. DuPont & Co.; and polyolefins having a density less than 0.93, including elastomeric ethylene-propylene copolymers, linear low density polyethylene (LLDPE), and linear low density polyethylene (LLDPE) containing maleic anhydride.

The preferred ethylene copolymers which can be used as component B include, but are not limited to, ethylene/butylacrylate/carbon monoxide (E/BA/CO), ethylene/methylacrylate (E/MA), ethylene/ethylacrylate (E/EA), ethylene/butylacrylate (E/BA), ethylene/vinylacetate (E/VA), ethylene/methacrylic acid (E/MAA or E/AA), ethylene/butylacrylate/methacrylic acid (E/BA/MAA or E/BA/AA), ethylene/methylacrylate/methacrylic acid (E/MA/MAA or E/MA/AA), ethylene/butylacrylate/maleic anhydride (E/BA/Manh), ethylene/ethylacrylate/maleic anhydride (E/EA/Manh) or ethylene/methylacrylate/maleic anhydride (E/MA/Manh). Where one of the α, β-ethylenically unsaturated monomers is an acid containing moiety, the polymer can be partially neutralized with an ion such as Na+, K+, Zn++, Mg++, Li+, Ca++, NH4+, or the like. The acid groups in the unsaturated mono-carboxylic acid are neutralized from 0–80 percent by at least one metal ion selected from this group of ions.

In one preferred alternate embodiment, the second, softening polymeric component can be modified with a silane coupling agent, such as vinyl silanes containing epoxide groups, by reacting the silane coupling agents with the softening polymeric component in a reactive extrusion process, through the addition of a peroxide such as dicumyl peroxide, available in polymerization agents containing dicumyl peroxide under the trademark "DI-CUP" from Aqualon Co of Wilmington, Del. The resultant modified reactive softening copolymer will bond with the first strong polymeric component when they are blended together. Other silicon containing vinyl monomers having functional groups such as amide, methoxy, epoxide, anhydride, and the like can also be reacted with the softening polymeric component by reactive extrusion with a peroxide such as dicumyl peroxide. The grafting of the vinyl silanes with the softening polymeric component can be carried out in conventional polymer processing equipment such as a single screw extruder, a twin screw extruder, a two roll mill, or a Henschel type of mixer, and the like. Catheters and balloons formed with the modified softening polymeric component according to the invention can be provided with enhanced flexibility, and can advantageously have reduced or eliminated requirements for the proportion of the third polymeric component, the compatibilizing agent, as such a modified softening polymeric component, such as a glycidyl or anhydride containing silicon vinyl monomer grafted acrylic ester polyolefin, can be at least in part be substituted for the third polymeric component, the compatibilizing agent. In one preferred alternate embodiment, when the silane coupling agent is utilized, the amount of the compatibilizing agent used is reduced to zero.

The third polymeric component, component C, is preferably an ethylene copolymer that functions as a compatibilizing agent, in that it forms a covalent bond with the first polymeric component, and can react with the Y' moiety of the second polymeric component when the Y' moiety is present, and blends compatibly with the second polymeric component. Component C preferably comprises from zero to about 40 percent of the total blend composition, and more preferably from about 1 to about 20 percent of the total blend composition. Component C can have the formula E/X/Y or E/Y, where E is about 55 to 96 percent by weight, X, if present, is from zero to about 40 percent by weight, and more preferably between zero and about 10 percent by weight, and Y is about 0.5 to 10 percent, and most preferably about 4 to 8 percent, by weight of the compatibilizing ethylene copolymer. In component C, E is ethylene; and X is an $\alpha$, $\beta$-ethylenically unsaturated monomer derived from at least one of alkylacrylate, alkylmethacrylate, alkyl vinyl ether, carbon dioxide, sulfur dioxide, or mixtures thereof, where the alkyl groups contain 1–12 carbon atoms, such as vinyl acetate, methylacrylate, butylacrylate, and methyl vinyl ether. More specifically, X can, for example, consist of a moiety derived from at least one alkyl acrylate, alkyl methacrylate, or mixtures thereof where the alkyl groups contain 1–8 carbon atoms. Y is an $\alpha$, $\beta$-ethylenically unsaturated monomer containing a reactive group, such as epoxide, anhydride, isocyanate, or oxazoline, for example, that forms a covalent bond with said first polymeric component. In one preferred embodiment, Y is selected from the group consisting of glycidyl methacrylate and glycidyl acrylate, maleic anhydride, and isocyanatoethylmethacrylate.

The fourth component, component D, also can optionally be included in the blend composition to serve as a catalyst to initiate a reaction between the compatibilizing agent and the second, softening polymeric component. In one currently preferred embodiment, the fourth component can comprise an aliphatic tertiary amine, believed to be an active catalytic ingredient. One commercial material currently preferred for use as the fourth, or catalytic component, is available under the trade name "LOTADER XX1275" from Elf Atochem, and is believed to comprise approximately 6 percent aliphatic tertiary amine, with the remainder of the ingredients comprising 2-propanoic acid, ethyl ester, ethylene, and 2,5-furandione. The aliphatic tertiary amine is believed to catalyze a reaction between moieties in the softening component and the compatibility component, such as between maleic anhydride (Manh) in the softening component, and glycidyl methacrylate (GMA) in the compatabilizing component, for example. Specific examples of aliphatic tertiary amines that may be suitable as the active catalytic ingredient in the catalytic component include, but are not limited to, benzyl dimethyl amine (BDMA), tri (dimethylamino methyl)phenol, boron trichloride amine complex, and boron trifluoride amine ($BF_3$ amine).

In one currently preferred embodiment, the first polymeric component of the balloon material blend comprises about 70 to 79 percent by weight PET as component A; about 10 to 20 percent by weight of the second polymeric, component B, comprising an ethylene copolymer having the formula E'X'Y', where E' is ethylene, and is about 65 to 84 percent by weight of the ethylene copolymer; and X' is selected from the group of methylacrylate, ethylacrylate, propylacrylate, and butylacrylate, and is about 15 to 30 percent by weight of the ethylene copolymer; and Y' is about 1 to 5 percent maleic anhydride; and about 4 to 15 percent by weight, of component C, which is an ethylene copolymer having the formula E/X/Y or E/Y, where E is ethylene, and is about 92 to 96 percent by weight of component C; X is from zero to about 10 percent by weight and is selected from a moiety derived from at least one of alkyl acrylate, alkyl methacrylate, alkyl vinyl ether, carbon monoxide, sulfur dioxide, or mixtures thereof; and Y is selected from the group consisting of glycidyl methacrylate, glycidyl ethylacrylate, and glycidyl butylacrylate, and is about 4 to 8 percent by weight of component C. The second polymeric component, component B, is most preferably an elastomeric ethylene copolymer selected from the group consisting of ethylene/methylacrylate, ethylene/ethylacrylate, ethylene/butylacrylate, ethylene/methylacrylate/maleic anhydride, ethylene/ethylacrylate/maleic anhydride, and ethylene/butylacrylate/maleic anhydride. The third polymeric component, component C, is most preferably ethylene glycidyl acrylate or glycidyl methacrylate, or mixtures thereof.

The blended polymeric material is typically pelletized, dried, and introduced into an extruder that typically can be set to extrude balloon dilatation catheter tubing having an inner diameter of about 0.018 to 0.020 inches and an outer diameter of about 0.036 0.040 inches. An exemplary extruder typically has several temperature controlled zones, including three zones in the barrel, and zones in the clamp and die of the extruder. The barrel and die temperatures of the extruder zones are typically set in zone 1 at about 370° to 405° F. in zone 2 at about 430° to 485° F., in zone 3 at 480° to 510° F., and the clamp and die 1 and 2 at about 480° to 510° F., as is described further hereinafter in the examples, and depending upon the specific melt temperature and properties of the blended polymeric material being used.

The balloon dilatation catheter tubing can then be further processed to form a balloon. While balloons can be freeblown, or manufactured by conventional methods such as those described in U.S. Pat. No. 4,411,055, incorporated by reference herein, the dilatation catheter balloons of the invention are currently preferably formed in a mold such as is illustrated in FIG. 1. The dilatation catheter tubing 10 is oriented in a blow molding apparatus 12, and is connected at one end to a source of pressurized gas 14. The other end of the tubing 16 which extends beyond the mold, can be clamped or otherwise sealed during pressurization of the tubing. The tubing can also be affixed to a tensioning device. The tubing within the mold is then heated to a desired temperature below the crystalline melting point of the tubing, such as until the material deforms, for example. During heating, or optionally after heating, pressurized gas is applied to the tubing, and optionally tension is also applied to the tubing, until the balloon 18 is formed, filling the desired interior shape of the mold. The balloon and tubing are then cooled to room temperature. The balloon is then removed from the mold, and can be further processed to construct a dilatation catheter.

In addition, in a preferred aspect of the invention, the dilatation catheter tubing material employed in making the balloons and catheters of the invention can advantageously be irradiated using ionizing radiation from an electron beam, gamma rays, ultraviolet light, or a molecular beam, to significantly alter the properties of the balloon material to provide improved balloon performance such as higher burst pressures. For example, where tubing formed of the balloon material was subjected to an electron beam of about 10–100 Mrads and energies of 10–20,000 kev, and balloons were formed using the previously described methods, higher balloon burst strengths and higher fatigue strengths were obtained from the balloon material.

The catheters and balloons of the invention provide balloon dilatation catheters with the ability to cross multiple lesions, good track, cross, and folding, low compliance with rated burst pressures of about 10–15 atm, and mean burst pressures of about 13–20 atm. Balloons made from the polymeric materials described also typically have a lower susceptibility to defects through mechanical handling than PET. When exposed to ionizing radiation to toughen the balloon material, the fatigue and burst strengths are substantially increased, to give rated burst pressures of 12–14 atm or greater, mean burst pressures of 17–20 atm, and a compliance of about 0.01–0.03 (mm/atm).

EXAMPLE 1

A polymer blend containing 80 weight percent PET Traytuf 9506C manufactured by Shell, and 20 weight percent ethylene ethylacrylate (EEA) DPDA 6182 manufactured by Union Carbide, was produced by compounding in a twin screw extruder set for low shear conditions. The PET and EEA were mixed in a weight ratio of 80/20. The PET/EEA mixture was loaded into the hopper of the compounder. The barrel temperatures were set to 410° F. in zone 1, 490° F. in zones 2 and 3, and 480° in zone four and at the head of the barrel, the screw speed was maintained at 150 RPM, and the material was pelletized. Balloon dilatation catheter tubing having an inner diameter of 0.018 inches and an outer diameter of 0.036 inches was extruded using the 80/20. PET/EEA blend. The 80/20. PET/EEA blended material was dried. The barrel and die temperatures of the extruder were set, with zone 1 at 390° F., zone 2 at 480° F., zone 3 at 500° F., and the clamp, die 1 and die 2 at 510° F. The melt temperature of the blend was 574° F. Examination with a scanning electron microscope of a portion of the blend before extrusion into balloon tubing showed that the EEA formed spherical particles with a diameter greater than one micron, with poor interfacial adhesion within the PET matrix. A section of the extruded balloon tubing was also examined with a scanning electron microscope, showing that the EEA formed tubules in the extruded balloon tubing that pulled out of the PET matrix. When balloons were formed from the tubing without irradiation, the balloons were found to have rupture strengths of about 194 psi (about 13.2 atm). When subjected to 10–100 Mrads of irradiation, balloons formed from the tubing were found to have increased rupture strengths to about 250 psi (about 17.0 atm).

EXAMPLE 2

The blend of PET and EEA from Example 1 was compounded and blended with 2 percent of the total blend composition by weight of a third component, E/EA/GMA, as a compatibilizer, available under the trade name "LOTADER AX8660" from Elf Atochem. Examination with a scanning electron microscope of a portion of the blend before extrusion into balloon tubing showed that the EEA formed a much better dispersion with better interfacial adhesion within the PET matrix, with little or no particle pullout from the PET matrix. A section of the extruded balloon tubing made from the blend was also examined with a scanning electron microscope, showing that the EEA formed no tubules in the extruded balloon tubing, and that the dispersed particles of EEA were well adhered to the PET matrix. The material had a burst pressure of about 50 psi higher than in Example 1.

EXAMPLES 3–10

Balloon material blends were also formed using PET available as Traytuf 9506C from Shell, with a tensile strength of 7000 psi (non-oriented), and 10000–12000 (oriented), an elongation of 400–500 percent (after yield), a flexural modulus of 500,000–600,000 psi, and a melting point of 257° C. EEA available as DPDA 6182 from Union Carbide was used in Examples 3–5 and 8–10, with a tensile strength of 2300 psi, elongation of 670 percent, a flexural modulus of 6400 psi, a melt index of 1.5, a durometer of 91A, a melting point of 85 C, a density of 0.93 and a Vicat Softening index of 64. EMAC available as TC130 from Exxon was used in Examples 6 and 7, with a tensile strength of 1200 psi, an elongation of 1600 percent, a flexural modulus of 300 psi, a melt index of 20, a Durometer of 85A, a melting point of 79 C, a density of 0.94 and a Vicat Softening index of 50. Lotryl 24MA005 (EMA) from Elf Atochem was used as the softening component in Example 10, with a tensile strength of 2910 psi, elongation of 700 percent, a melt index of 0.5, a Durometer of 84A, a melting point of 70 C, and a Vicat Softening index of 43. LOTADER AX8660 (67 percent E, 25 percent EA, 8 percent GMA) from Elf Atochem was used as the compatibilizing agent in Examples 4–10, with a tensile strength of 509 psi, an elongation of 700 percent, a melt index of 6.0, a Durometer of 60A, a melting point of 63 C, and a Vicat Softening index of 34.

The blend compositions of Examples 3–10 are listed in Table I below, and were compounded under the compounding conditions noted in Table II and were extruded under the tubing extrusion conditions noted in Table III.

TABLE I

| Example | PET % | EEA % | EMAC % | Lotryl % | Lotader % |
|---|---|---|---|---|---|
| 3 | 60 | 40 | — | — | — |
| 4 | 78.4 | 19.6 | — | — | 2 |
| 5 | 76 | 19 | — | — | 5 |
| 6 | 78.4 | — | 19.6 | — | 2 |
| 7 | 76 | — | 19 | — | 5 |
| 8 | 68.8 | 29.5 | — | — | 1.7 |
| 9 | 59.1 | 39.4 | — | — | 1.5 |
| 10 | 70 | — | — | 28 | 2 |

TABLE II

| Example | 3 | 4 | 5 | 6 | 7 | 8 | 9 | 10 |
|---|---|---|---|---|---|---|---|---|
| T1 °F. | 410 | 410 | 410 | 400 | 400 | 400 | 400 | 275 |
| T2 °F. | 490 | 480 | 480 | 480 | 480 | 450 | 450 | 480 |
| T3 °F. | 490 | 480 | 480 | 490 | 490 | 485 | 485 | 535 |
| T4 °F. | 480 | 500 | 500 | 515 | 515 | 500 | 500 | 555 |
| Thead °F. | 480 | 500 | 500 | 515 | 515 | 500 | 500 | 555 |
| RPM | 150 | 150 | 150 | 150 | 150 | 150 | 150 | 150 |

TABLE III

| Example | 3 | 4 | 5 | 6 | 8 | 10 |
|---|---|---|---|---|---|---|
| T1 °F. | 390 | 400 | 400 | 370 | 400 | 405 |
| T2 °F. | 480 | 480 | 480 | 430 | 480 | 485 |
| T3 °F. | 500 | 510 | 510 | 480 | 500 | 490 |
| Tclamp °F. | 510 | 510 | 510 | 480 | 500 | 490 |
| Tdie1 °F. | 510 | 510 | 510 | 480 | 500 | 490 |
| Tdie2 °F. | 510 | 510 | 510 | 480 | 500 | 500 |
| I.D. inches | .018 | .020 | .020 | .020 | .020 | .020 |
| O.D. inches | .036 | .040 | .040 | .040 | .040 | .040 |
| Dry °F. | 150 | 150 | 150 | 150 | 150 | 150 |

EXAMPLE 11

In Example 11, a blend composition was compounded according to the method of Example 1. Catheter tubing was extruded with an inner diameter of 0.018 inches, and an outer diameter of 0.036 inches. The tubing was subjected to 25 Mrads of radiation. Balloons were formed with an inflated outer diameter of 0.1135 inches and a doublewall thickness (DWT) of 0.00135 inches and had a mean burst pressure of 250 psi.

EXAMPLES 12–13

In Examples 12 and 13, a blend composition was compounded according to the method of Example 2. In Example 12, catheter tubing was extruded with an inner diameter of 0.020 inches and an outer diameter of 0.040 inches. Tubing was subjected to 40 Mrads of irradiation. Dilatation balloons were formed with an outer diameter of 0.119 in., a DWT of 0.0015 in., and had a mean burst pressure of 285 psi (19.4 atm). Tubing not subjected to irradiation was formed into a balloon with an outer diameter of 0.1195 in., a DWT of 0.00145 in., and had a lower mean burst pressure of 252 psi (17.1 atm).

EXAMPLES 14–15

In Examples 14 and 15, a polymer blend containing 90 weight percent PET Traytuf 9506C manufactured by Shell, and 10 weight percent of an ionomeric resin of ethylene and methacrylic acid, available under the tradename "SURLYN," manufactured by DuPont, were blended. The materials were separately dried. Balloon tubing having an inner diameter of 0.021 inches and an outer diameter of 0.0325 inches was extruded using this 90/10 blend. The barrel and die temperatures of the extruder were set with Zone 1 at 460° F., Zone 2 at 485° F., Zone 3 at 500° F., die 1 at 520° F., die 2 at 520° F.

In Example 14, a balloon was formed and material had a mean burst pressure of 207 psi (14.1 atm).

In Example 15, tubing was formed as in Example 13. The tubing was subjected to 20 Mrads of radiation. The balloons formed had a mean burst pressure of 255 psi (17.3 atm).

EXAMPLE 16

A two component polymer blend containing 80 weight percent PET, as in Example 1 above, and 20 weight percent ethylene/ ethylacrylate/maleic anhydride (E/EA/Manh), available under the trade name "LOTADER 4700" from Elf Atochem, was compounded as above. The PET and E/EA/Manh were mixed in a weight ratio of 80/20, with no compatibilizer, and formed into balloons. The balloons were tested, and found to have rupture strengths of about 170 psi (about 11.6 atm).

EXAMPLE 17

Another two component polymer blend containing 80 weight percent PET, and 20 weight percent ethylene/ glycidyl methacrylate (E/GMA), available as LOTADER AX8840 from Elf Atochem, was compounded as above. The PET and E/GMA were mixed in a weight ratio of 80/20, with no softening polymer component, and formed into balloons. Examination with a scanning electron microscope showed small particle sizes with cross-sectional dimensions of less than 1 μm.

EXAMPLE 18

Another two component polymer blend containing 70 weight percent PET, and 30 weight percent ethylene/ glycidyl methacrylate (E/GMA), available as LOTADER AX8840 from Elf Atochem, was compounded as above. The PET and were mixed in a weight ratio of 70/30, with no compatibilizer, and formed into balloons. Examination with a scanning electron microscope showed small particle sizes with cross-sectional dimensions of less than 1 μm.

EXAMPLE 19

A three component polymer blend was compounded, of 80 weight percent PET, 18 weight percent ethylene/ ethylacrylate/maleic anhydride (E/EA/Manh), available as LOTADER 4700 from Elf Atochem, and 2 weight percent ethylene/ethylacrylate/glycidyl methacrylate (E/EA/GMA), available as LOTADER AX8660 from Elf Atochem.

EXAMPLE 20

Another three component polymer blend was compounded of 80 weight percent PET as in Example 1, 18 weight percent ethylene/ ethylacrylate/maleic anhydride (E/EA/Manh), available as LOTADER 4700 from Elf Atochem, and 2 weight percent ethylene/glycidyl methacrylate (E/GMA), available as LOTADER AX8840 from Elf Atochem. Balloons were formed from the blend, tested, and found to have rupture strengths of about 156 psi (about 10.3 atm).

EXAMPLE 21

Another three component polymer blend was compounded, of 78 weight percent PET, 15 weight percent ethylene/ethylacrylate/maleic anhydride (E/EA/Manh), available as LOTADER 4700 from Elf Atochem, and 7 weight percent ethylene/glycidyl methacrylate (E/GMA), available as LOTADER AX8840 from Elf Atochem, and formed into balloons.

EXAMPLE 22

A four component polymer blend was compounded of 80 weight percent PET as in Example 1, 14 weight percent ethylene/ethylacrylate/ maleic anhydride (E/EA/Manh), available as LOTADER 4700 from Elf Atochem, 4 weight percent ethylene/glycidyl methacrylate (E/GMA), available as LOTADER AX8840 from Elf Atochem, and 2 weight percent of a fourth component containing a catalyst, available as LOTADER XX1275 from Elf Atochem. Unirradiated balloons were formed from the blend, tested, and found to have rupture strengths of about 228 psi (about 15.5 atm). Tubing was subjected to 30 Mrads of irradiation, and the balloons were formed using the following balloon forming parameters: the temperature of the balloon blowing apparatus was set to about 280° to 300°F.; a pressure of about 135 to 175 psi; and a tension of about 25 to 100 grams. The balloons were found to have rupture strengths of about 277 psi (about 18.8 atm). Micrographs of the balloon material showed that the blend exhibited small particle sizes, generally smaller than about 2 μm.

EXAMPLE 23

Another four component polymer blend was compounded, of 80 weight percent PET, 14 weight percent ethylene/ ethylacrylate/maleic anhydride (E/EA/Manh), available as LOTADER 4700 from Elf Atochem, 4 weight percent ethylene/ethylacrylate/glycidyl methacrylate (E/EA/GMA), available as LOTADER AX8660 from Elf Atochem, and 2 weight percent of a fourth component containing a catalyst, available as LOTADER XX1275 from Elf Atochem.

EXAMPLE 24

Another four component polymer blend was compounded, of 80 weight percent PET, 16 weight percent ethylene/ ethylacrylate/maleic anhydride (E/EA/Manh), available as LOTADER 4700 from Elf Atochem, 2 weight percent ethylene/ethylacrylate/ glycidyl methacrylate (E/EA/GMA), available as LOTADER AX8660 from Elf Atochem, and 2 weight percent of a fourth component containing a catalyst, available as LOTADER XX1275 from Elf Atochem.

EXAMPLE 25

Another four component polymer blend was compounded, of 80 weight percent PET, 10 weight percent ethylene/ ethylacrylate/maleic anhydride (E/EA/Manh), available as LOTADER 4700 from Elf Atochem, 8 weight percent ethylene/glycidyl methacrylate (E/GMA), available as LOTADER AX8840 from Elf Atochem, and 2.0 weight percent of a fourth component containing a catalyst, available as LOTADER XX1275 from Elf Atochem. Balloons formed from the tubing without irradiation were found to have rupture strengths of about 250 psi (about 17.0 atm). When subjected to 10–100 Mrads of irradiation, balloons formed from the tubing were found to have increased rupture strengths of about 282 psi (about 19.2 atm).

EXAMPLE 26

Another four component polymer blend was compounded, of 78 weight percent PET, 8 weight percent ethylene/ ethylacrylate/maleic anhydride (E/EA/Manh), available as LOTADER 4700 from Elf Atochem, 12 weight percent ethylene/glycidyl methacrylate (E/GMA), available as LOTADER AX8840 from Elf Atochem, and 2.0 weight percent of a fourth component containing a catalyst, available as LOTADER XX1275 from Elf Atochem. Balloons formed from tubing made from this blend, without irradiation, were found to have rupture pressures of approximately 287 psi (19.5 atm).

EXAMPLE 27

Another four component polymer blend was compounded, of 78 weight percent PET, 12 weight percent ethylene/ ethylacrylate/maleic anhydride (E/EA/Manh), available as LOTADER 4700 from Elf Atochem, 8 weight percent ethylene/glycidyl methacrylate (E/GMA), available as LOTADER AX8840 from Elf Atochem, and 2.0 weight percent of a fourth component containing a catalyst, available as LOTADER XX1275 from Elf Atochem. Balloons formed from the tubing without irradiation were found to have rupture strengths of about 255 psi (about 17.3 atm). When subjected to 10–100 Mrads of irradiation, balloons formed from the tubing were found to have increased rupture strengths of about 291 psi (about 19.8 atm).

Figure 2:
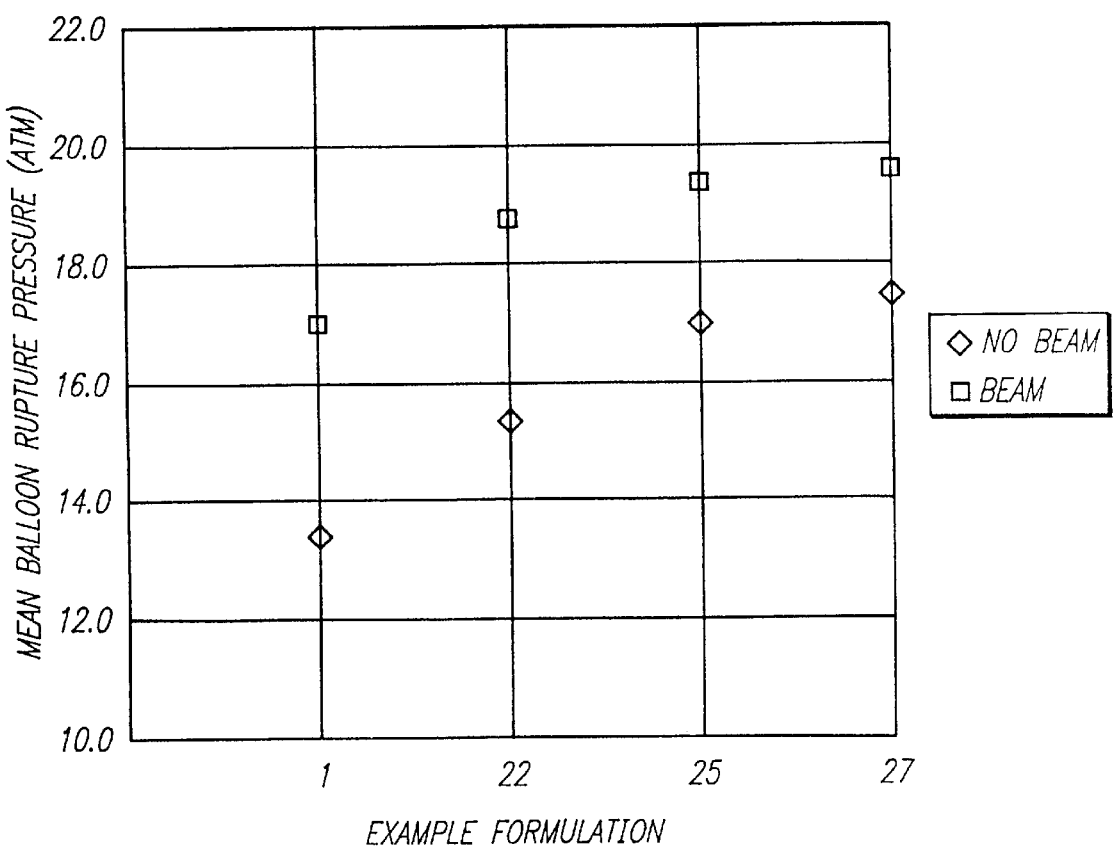
FIG. 2 is a chart illustrating the enhancement of balloon rupture pressure properties by irradiation with electron beam radiation.

FIG. 2, showing a chart of the mean balloon rupture pressure (atm) of unirradiated and irradiated balloons from Examples 1, 22, 25 and 27, illustrates the general improvement in rupture strengths of balloons made and irradiated according to the invention over unirradiated balloons, amounting to an average improvement of rupture strength due to irradiation of approximately 3 atm. Given that the dominant phase is relatively unaffected by radiation, such improvements in rupture strengths were surprising and unexpected.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A catheter member formed from a polymeric material, comprising:

about 70 to 79 percent by weight of the total polymeric material composition of a first polymeric component selected from the group consisting of polyesters and polyamides, said polyesters being prepared from the group of dicarboxylic acids selected from aromatic dicarboxylic acids having from 8 to 14 carbon atoms and aliphatic dicarboxylic acids having from 2 to 12 carbon atoms, and mixtures thereof, and at least one glycol selected from the group consisting of glycols having the formula $HO(CH_2)_nOH$, where n is an integer from 2 to 10, neopentyl glycol and cyclohexane dimethanol, and mixtures thereof, and said polyamides being branched or straight chain polyamides having a molecular weight of at least 5000, and mixtures thereof;

about 10 to 20 percent by weight of the total polymeric material composition of a second polymeric component having a Shore hardness less than 75 D, wherein said second polymeric component is a softening ethylene copolymer, and the ethylene copolymer has the formula E'X' or E'X'Y', where E' is ethylene, and is about 60 to 90 percent by weight of the ethylene copolymer, and where X' is about 10 to 40 percent by weight of the ethylene copolymer, and X' is selected from the group consisting of methylacrylate, ethylacrylate, propylacrylate, butylacrylate, and mixtures thereof, and Y', if present, is selected from the group consisting of α, β-ethylenically unsaturated monocarboxylic acids, α, β-ethylenically unsaturated dicarboxylic acids, and anhydrides, and mixtures thereof, comprising from zero to about 15 percent by weight of the ethylene copolymer; and from zero to about 40 percent by weight of the total polymeric material composition of a compatibilizing ethylene copolymer selected from the group of ethylene copolymers having the formula E/X/Y or E/Y, where E is ethylene,
- X is an α, β-ethylenically unsaturated monomer derived from at least one of alkylacrylate, alkylmethacrylate, alkyl vinyl ether, carbon monoxide, sulfur dioxide, where the alkyl groups contain 1 to 12 carbon atoms, and mixtures thereof, and
- Y is an α, β-ethylenically unsaturated monomer containing a reactive group that forms a covalent bond with said first polymeric component, wherein the sum of all the polymeric components is 100 weight percent.

2. The catheter member of claim 1, wherein said first polymeric component is selected from the group consisting of polyethylene-terephthalate, polybutylene-terephthalate, glycol modified polyethylene-terephthalate, 1,4-cyclohexylene dimethylene terephthalate/isophthalate copolymer, linear homopolymer esters derived from aromatic dicarboxylic acids and glycols of the general formula $HO(CH_2)_nOH$ where n is an integer from 2 to 10, and mixtures thereof 3. The catheter member of claim 1, wherein said first polymeric component is a polyester with glycol segments selected from the group consisting of ethylene glycol; 1,6-hexamethylene glycol; 1,8-octamethylene glycol; 1,10-decamethylene glycol; 2,2-dimethyl- 1,3-propane diol; 1,3-propylene glycol; 1,4-butylene glycol; neopentyl glycol and cyclohexane dimethanol, and mixtures thereof.

4. The catheter member of claim 1, wherein E' is about 65 to 84 percent by weight of the ethylene copolymer, X' is about 15 to 30 percent by weight of the ethylene copolymer, and Y' is maleic anhydride and is about 1 to 5 percent of the ethylene copolymer.

5. The catheter member of claim 1, wherein Y is an α, β-ethylenically unsaturated monomer containing a reactive group selected from the group consisting of epoxide, anhydride, isocyanate, or oxazoline, and mixtures thereof.

6. The catheter member of claim 1, wherein X is selected from the group consisting of vinyl acetate, methylacrylate, ethylacrylate, butylacrylate, and methyl vinyl ether, and mixtures thereof.

7. The catheter member of claim 1, wherein Y is selected from the group consisting of glycidyl methacrylate, glycidyl acrylate, maleic anhydride, and isocyanato-ethylmethacrylate, and mixtures thereof.

8. The catheter member of claim 1, wherein X is a moiety derived from at least one alkyl acrylate, alkyl methacrylate, or mixtures thereof, where the alkyl groups contain 1 to 8 carbon atoms.

9. The catheter member of claim 1, wherein Y is selected from the group consisting of glycidyl acrylate, glycidyl methacrylate, and epoxide containing copolymerizable monomers, and mixtures thereof.

10. The catheter member of claim 1, wherein E is ethylene, and is 55 to 96 percent by weight of the compatibilizing ethylene copolymer; X is selected from the group of methylacrylate, ethylacrylate and butylacrylate, and mixtures thereof, and is zero to about 40 percent by weight of the compatibilizing ethylene copolymer; and Y is selected from the group consisting of glycidyl acrylate and glycidyl methacrylate, and mixtures thereof, and is about 0.5 to 10 percent by weight of the compatibilizing ethylene copolymer.

11. The catheter member of claim 10, wherein X is from zero to about 10 percent by weight of the compatibilizing ethylene copolymer.

12. The catheter member of claim 10, wherein E is about 92 to 96 percent by weight of the compatibilizing ethylene copolymer, X is zero to 10 percent, and Y is about 4 to 8 percent by weight of the compatibilizing ethylene copolymer.

13. The catheter member of claim 1, wherein said polymeric material forming said catheter member is irradiated.

14. The catheter member of claim 13, wherein said polymeric material is irradiated using ionizing radiation generated by any of an electron beam, gamma rays, ultraviolet light, or a molecular beam.

15. The catheter member of claim 13, wherein said polymeric material is irradiated by an electron beam in the range of about 10 to 100 Mrads.

16. The catheter member of claim 1, wherein said polymeric material further includes a catalyst to catalyze a reaction between the compatibilizing ethylene copolymer and the second polymeric component.

17. The catheter member of claim 16, wherein the catalyst comprises an aliphatic tertiary amine.

18. A dilatation catheter balloon formed from a polymeric material comprising:
- about 70 to 79 percent by weight of the total polymeric material composition of a first polymeric component selected from the group consisting of polyesters, said polyesters being prepared from the group of dicarboxylic acids selected from aromatic dicarboxylic acids having from 8 to 14 carbon atoms and aliphatic dicarboxylic acids having from 2 to 12 carbon atoms, and mixtures thereof, and at least one glycol selected from the group consisting of glycols having the formula $HO(CH_2)_nOH$, where n is an integer from 2 to 10, neopentyl glycol and cyclohexane dimethanol, and mixtures thereof;
- about 10 to 20 percent by weight of the total polymeric material composition of a second polymeric component having a Shore hardness less than 75 D, wherein said second polymeric component is a softening ethylene copolymer, and the ethylene copolymer has the formula E'X' or E'X'Y', where E' is ethylene, and is about 60 to 90 percent by weight of the ethylene copolymer, and where X' is about 10 to 40 percent by weight of the ethylene copolymer, and X' is selected from the group consisting of methylacrylate, ethylacrylate, propylacrylate, butylacrylate, and mixtures thereof, and Y', if present, is selected from the group consisting of α, β-ethylenically unsaturated monocarboxylic acids, α, β-ethylenically unsaturated dicarboxylic acids, and anhydrides, and mixtures thereof, comprising from zero to about 15 percent by weight of the ethylene copolymer; and
- from zero to about 40 percent by weight of the total polymeric material composition of a compatibilizing ethylene copolymer selected from the group of ethylene copolymers having the formula E/X/Y or E/Y, where E is ethylene, X is an α, β-ethylenically unsaturated monomer derived from at least one of alkylacrylate, alkylmethacrylate, alkyl vinyl ether, carbon monoxide, sulfur dioxide, or mixtures thereof, where the alkyl groups contain 1 to 12 carbon atoms, and Y is an α, β-ethylenically unsaturated monomer containing a reactive group that forms a covalent bond with said first polymeric component, and mixtures thereof, wherein the sum of all the polymeric components is 100 weight percent.

19. The dilatation catheter balloon of claim 18, wherein said first polymeric component comprises about 70 to 79 percent of the total polymeric material composition, and is selected from the group consisting of polyethylene-terephthalate, polybutylene-terephthalate, glycol modified polyethylene-terephthalate, 1,4-cyclohexylene dimethylene terephthalate/isophthalate copolymer, linear homopolymer esters derived from aromatic dicarboxylic acids and glycols of the general formula $HO(CH_2)_nOH$ where n is an integer from 2 to 10, and mixtures thereof.

20. The dilatation catheter balloon of claim 18, wherein said first polymeric component is a polyester with glycol segments selected from the group consisting of ethylene glycol; 1,6-hexamethyleneglycol; 1,8-octamethylene glycol; 1,10-decamethylene glycol; 2,2-dimethyl-1,3-propane diol; 1,3- propylene glycol; 1,4- butylene glycol; neopentyl glycol and cyclohexane dimethanol, and mixtures thereof.

21. The dilatation catheter balloon of claim 18, wherein Y is an α, β-ethylenically unsaturated monomer containing a reactive group selected from the group consisting of epoxide, anhydride, isocyanate, or oxazoline, and mixtures thereof.

22. The dilatation catheter balloon of claim 18, wherein X is selected from the group consisting of vinyl acetate, methylacrylate, ethylacrylate, butylacrylate, and methyl vinyl ether, and mixtures thereof.

23. The dilatation catheter balloon of claim 18, wherein Y is selected from the group consisting of glycidyl methacrylate, glycidyl acrylate, maleic anhydride, and isocyanato-ethylmethacrylate, and mixtures thereof.

24. The dilatation catheter balloon of claim 18, wherein X is a moiety derived from at least one alkyl acrylate, alkyl methacrylate, or mixtures thereof, where the alkyl groups contain 1 to 8 carbon atoms.

25. The dilatation catheter balloon of claim 18, wherein Y is selected from the group consisting of glycidyl acrylate, glycidyl methacrylate, and epoxide containing copolymerizable monomers, and mixtures thereof.

26. The dilatation catheter balloon of claim 18, wherein E is ethylene, and is 55 to 96 percent by weight of the compatibilizing ethylene copolymer; X is selected from the group of methylacrylate, ethylacrylate and butylacrylate, and mixtures thereof, and is zero to about 40 percent by weight of the compatibilizing ethylene copolymer; and Y is selected from the group consisting of glycidyl acrylate and glycidyl methacrylate, and mixtures thereof, and is about 0.5 to 10 percent by weight of the compatibilizing ethylene copolymer.

27. The dilatation catheter balloon of claim 26, wherein X is from zero to about 10 percent by weight of the compatibilizing ethylene copolymer.

28. The dilatation catheter balloon of claim 26, wherein E is about 92 to 96 percent by weight of the compatibilizing ethylene copolymer, X is zero to 10 percent, and Y is about 4 to 8 percent by weight of the compatibilizing ethylene copolymer.

29. The dilatation catheter balloon of claim 18, wherein said polymeric material forming said dilatation catheter balloon is irradiated.

30. The dilatation catheter balloon of claim 29, wherein said polymeric material is irradiated using ionizing radiation generated by any of an electron beam, gamma rays, ultraviolet light, or a molecular beam.

31. The dilatation catheter balloon of claim 29, wherein said polymeric material is irradiated by an electron beam in the range of about 10 to 100 Mrads.

32. The dilatation catheter balloon of claim 18, wherein said polymeric material further includes a catalyst to catalyze a reaction between the compatibilizing ethylene copolymer and the second polymeric component.

33. The dilatation catheter balloon of claim 32, wherein the catalyst comprises an aliphatic tertiary amine.

34. The dilatation catheter balloon of claim 18, wherein E' is about 65 to 84 percent by weight of the ethylene copolymer, X' is about 15 to 30 percent by weight of the ethylene copolymer, and Y' is maleic anhydride and is about 1 to 5 percent of the ethylene copolymer.

35. A catheter member formed from a polymeric material, comprising:

about 60 to 79 percent by weight of the total polymeric material composition of a first polymeric component selected from the group consisting of polyesters and polyamides, said polyesters being prepared from the group of dicarboxylic acids selected from aromatic dicarboxylic acids having from 8 to 14 carbon atoms and aliphatic dicarboxylic acids having from 2 to 12 carbon atoms, and mixtures thereof, and at least one glycol selected from the group consisting of glycols having the formula $HO(CH_2)_nOH$, where n is an integer from 2 to 10, neopentyl glycol and cyclohexane dimethanol, and mixtures thereof, and said polyamides being branched or straight chain polyamides having a molecular weight of at least 5000, and mixtures thereof;

about 10 to 40 percent by weight of the total polymeric material composition of a second polymeric component having a Shore hardness less than 75 D, wherein said second polymeric component is a softening ethylene copolymer, and the ethylene copolymer is selected from the group consisting of ethylene/butylacrylate/carbon monoxide, ethylene/methylacrylate, ethylene/ethylacrylate, ethylene/butylacrylate, ethylene/vinylacetate, ethylene/methacrylic acid, ethylene/butylacrylate/methacrylic acid, ethylene/methylacrylate/methacrylic acid, ethylene/methylacrylate/maleic anhydride, ethylene/ethyl acrylate/maleic anhydride, and ethylene/butylacrylate/maleic anhydride, and mixtures thereof; and from zero to about 40 percent by weight of the total polymeric material composition of a compatibilizing ethylene copolymer selected from the group of ethylene copolymers having the formula E/X/Y or E/Y, where E is ethylene, X is an α, β-ethylenically unsaturated monomer derived from at least one of alkylacrylate, alkylmethacrylate, alkyl vinyl ether, carbon monoxide, sulfur dioxide, where the alkyl groups contain 1 to 12 carbon atoms, and mixtures thereof, and Y is an α, β-ethylenically unsaturated monomer containing a reactive group that forms a covalent bond with said first polymeric component, wherein the sum of all the polymeric components is 100 weight percent.

36. A catheter member formed from a polymeric material, comprising:

about 60 to 79 percent by weight of the total polymeric material composition of a first polymeric component selected from the group consisting of polyesters and polyamides, said polyesters being prepared from the group of dicarboxylic acids selected from aromatic dicarboxylic acids having from 8 to 14 carbon atoms and aliphatic dicarboxylic acids having from 2 to 12 carbon atoms, and mixtures thereof, and at least one glycol selected from the group consisting of glycols having the formula $HO(CH_2)_nOH$, where n is an integer from 2 to 10, neopentyl glycol and cyclohexane dimethanol, and mixtures thereof, and said polyamides being branched or straight chain polyamides having a molecular weight of at least 5000, and mixtures thereof;

about 10 to 40 percent by weight of the total polymeric material composition of a second polymeric component having a Shore hardness less than 75 D, wherein said second polymeric component is a softening ethylene copolymer, and said softening ethylene copolymer contains ethylene and at least one other monomer selected from the group consisting of α, β-ethylenically unsaturated monomers, carbon monoxide, and sulfur dioxide, and mixtures thereof, and wherein one of the α, β-ethylenically unsaturated monomers is an acid containing moiety, and the polymer is partially neutralized with an ion selected from the group of sodium, potassium, zinc, magnesium, lithium, calcium, and ammonium, and mixtures thereof; and from zero to about 40 percent by weight of the total polymeric material composition of a compatibilizing ethylene copolymer selected from the group of ethylene copolymers having the formula E/X/Y or E/Y, where E is ethylene, X is an α, β-ethylenically unsaturated monomer derived from at least one of alkylacrylate, alkylmethacrylate, alkyl vinyl ether, carbon monoxide, sulfur dioxide, where the alkyl groups contain 1 to 12 carbon atoms, and mixtures thereof, and Y is an α, β-ethylenically unsaturated monomer containing a reactive group that forms a covalent bond with said first polymeric component, wherein the sum of all the polymeric components is 100 weight percent.

37. A catheter member formed from a polymeric material, comprising:

about 70 to 79 percent by weight of the total polymeric material composition of a first polymeric component selected from the group consisting of polyesters and polyamides, said polyesters being prepared from the group of dicarboxylic acids selected from aromatic dicarboxylic acids having from 8 to 14 carbon atoms and aliphatic dicarboxylic acids having from 2 to 12 carbon atoms, and mixtures thereof, and at least one glycol selected from the group consisting of glycols having the formula $HO(CH_2)_nOH$, where n is an integer from 2 to 10, neopentyl glycol and cyclohexane dimethanol, and mixtures thereof, and said polyamides being branched or straight chain polyamides having a molecular weight of at least 5000, and mixtures thereof;

about 10 to 20 percent by weight of the total polymeric material composition of a second polymeric component having a Shore hardness less than 75 D, wherein said second polymeric component is a softening ethylene copolymer, and the ethylene copolymer has the formula E'X' or E'X'Y', where E' is ethylene, and is about 60 to 90 percent by weight of the ethylene copolymer, and where X' is about 10 to 40 percent by weight of the ethylene copolymer, and X' is selected from the group consisting of methylacrylate, ethylacrylate, propylacrylate, butylacrylate, and mixtures thereof, and Y', if present, is selected from the group consisting of α, β-ethylenically unsaturated monocarboxylic acids, α, β-ethylenically unsaturated dicarboxylic acids, and anhydrides, and mixtures thereof, comprising from zero to about 15 percent by weight of the ethylene copolymer, and wherein said second polymeric component includes a vinyl silane coupling agent containing a functional group selected from the group consisting of amide, methoxy, epoxide, and anhydride, and combinations thereof, whereby said second polymeric component forms a bond with said first polymeric component, and wherein the sum of all the polymeric components is 100 weight percent.

38. A dilatation catheter balloon formed from a polymeric material comprising:

about 60 to 79 percent by weight of the total polymeric material composition of a first polymeric component selected from the group consisting of polyesters, said polyesters being prepared from the group of dicarboxylic acids selected from aromatic dicarboxylic acids having from 8 to 14 carbon atoms and aliphatic dicarboxylic acids having from 2 to 12 carbon atoms, and mixtures thereof, and at least one glycol selected from the group consisting of glycols having the formula $HO(CH_2)_nOH$, where n is an integer from 2 to 10, neopentyl glycol and cyclohexane dimethanol, and mixtures thereof;

about 10 to 40 percent by weight of the total polymeric material composition of a second polymeric component having a Shore hardness less than 75 D, wherein said second polymeric component is a softening ethylene copolymer, and the ethylene copolymer is selected from the group consisting of ethylene/butylacrylate/ carbon monoxide, ethylene/methylacrylate, ethylene/ ethylacrylate, ethylene/butylacrylate, ethylene/ vinylacetate, ethylene/methacrylic acid, ethylene/ butylacrylate/methacrylic acid, ethylene/ methylacrylate/methacrylic acid, ethylene/ methylacrylate/maleic anhydride, ethylene/ ethylacrylate/maleic anhydride, and ethylene/ butylacrylate/maleic anhydride, and mixtures thereof; and from zero to about 40 percent by weight of the total polymeric material composition of a compatibilizing ethylene copolymer selected from the group of ethylene copolymers having the formula E/X/Y or E/Y, where E is ethylene, X is an α, β-ethylenically unsaturated monomer derived from at least one of alkylacrylate, alkylmethacrylate, alkyl vinyl ether, carbon monoxide, sulfur dioxide, or mixtures thereof, where the alkyl groups contain 1 to 12 carbon atoms, and Y is an α, β-ethylenically unsaturated monomer containing a reactive group that forms a covalent bond with said first polymeric component, and mixtures thereof, wherein the sum of all the polymeric components is 100 weight percent.

39. A dilatation catheter balloon formed from a polymeric material comprising:

about 70 to 79 percent by weight of the total polymeric material composition of a first polymeric component selected from the group consisting of polyesters, said polyesters being prepared from the group of dicarboxylic acids selected from aromatic dicarboxylic acids having from 8 to 14 carbon atoms and aliphatic dicarboxylic acids having from 2 to 12 carbon atoms, and mixtures thereof, and at least one glycol selected from the group consisting of glycols having the formula $HO(CH_2)_nOH$, where n is an integer from 2 to 10, neopentyl glycol and cyclohexane dimethanol, and mixtures thereof;

about 10 to 40 percent by weight of the total polymeric material composition of a second polymeric component having a Shore hardness less than 75 D, wherein said second polymeric component is a softening ethylene copolymer, and said softening ethylene copolymer contains ethylene and at least one other monomer selected from the group consisting of α, β-ethylenically unsaturated monomers, carbon monoxide, and sulfur dioxide, and mixtures thereof, and wherein one of the α, β-ethylenically unsaturated monomers is an acid containing moiety, and the polymer is partially neutralized with an ion selected from the group of sodium, potassium, zinc, magnesium, lithium, calcium, and ammonium, and mixtures thereof; and from zero to about 40 percent by weight of the total polymeric material composition of a compatibilizing ethylene copolymer selected from the group of ethylene copolymers having the formula E/X/Y or E/Y, where E is ethylene, X is an α, β-ethylenically unsaturated monomer derived from at least one of alkylacrylate, alkylmethacrylate, alkyl vinyl ether, carbon monoxide, sulfur dioxide, or mixtures thereof, where the alkyl groups contain 1 to 12 carbon atoms, and Y is an α, β-ethylenically unsaturated monomer containing a reactive group that forms a covalent bond with said first polymeric component, and mixtures thereof, wherein the sum of all the polymeric components is 100 weight percent.

40. A dilatation catheter balloon formed from a polymeric material comprising:

about 70 to 79 percent by weight of the total polymeric material composition of a first polymeric component selected from the group consisting of polyesters, said polyesters being prepared from the group of dicarboxylic acids selected from aromatic dicarboxylic acids having from 8 to 14 carbon atoms and aliphatic dicarboxylic acids having from 2 to 12 carbon atoms, and mixtures thereof, and at least one glycol selected from the group consisting of glycols having the formula $HO(CH_2)_nOH$, where n is an integer from 2 to 10, neopentyl glycol and cyclohexane dimethanol, and mixtures thereof;

about 10 to 20 percent by weight of the total polymeric material composition of a second polymeric component having a Shore hardness less than 75 D, wherein said second polymeric component is a softening ethylene copolymer, and the ethylene copolymer has the formula E'X' or E'X'Y', where E' is ethylene, and is about 60 to 90 percent by weight of the ethylene copolymer, and where X' is about 10 to 40 percent by weight of the ethylene copolymer, and X' is selected from the group consisting of methylacrylate, ethylacrylate, propylacrylate, butylacrylate, and mixtures thereof, and Y', if present, is selected from the group consisting of α, β-ethylenically unsaturated monocarboxylic acids, α, β-ethylenically unsaturated dicarboxylic acids, and anhydrides, and mixtures thereof, comprising from zero to about 15 percent by weight of the ethylene copolymer, wherein said second polymeric component includes a vinyl silane coupling agent containing a functional group selected from the group consisting of amide, methoxy, epoxide, and anhydride, and combinations thereof, whereby said second polymeric component forms a bond with said first polymeric component, and wherein the sum of all the polymeric components is 100 weight percent.

* * * * *